(12) United States Patent
Juranas

(10) Patent No.: US 6,368,872 B1
(45) Date of Patent: Apr. 9, 2002

(54) APPARATUS AND METHOD FOR CHEMICAL PROCESSING

(75) Inventor: David L. Juranas, Bahama, NC (US)

(73) Assignee: TECAN Trading AG, Männedorf (CH)

( * ) Notice: Subject to any disclaimer, the term of this patent is extended or adjusted under 35 U.S.C. 154(b) by 0 days.

(21) Appl. No.: 09/426,168

(22) Filed: Oct. 22, 1999

(51) Int. Cl.⁷ .......................... G01N 1/10; G01N 35/00; G01N 33/48; B01L 3/02; B32B 27/04
(52) U.S. Cl. .......................... 436/180; 436/43; 436/49; 422/100; 422/63; 422/65; 422/68.1; 414/416.01
(58) Field of Search ................. 422/100, 101, 422/102, 63, 65, 68.1; 414/416.01, 416.08; 198/377.01, 377.02, 408; 436/43, 49, 180

(56) References Cited

U.S. PATENT DOCUMENTS

| | | | |
|---|---|---|---|
| 2,642,212 A | * 6/1953 | Currivan | 198/377.01 |
| 3,061,071 A | * 10/1962 | Roehrbein | 498/377.01 |
| 3,736,099 A | 5/1973 | Begg et al. | 23/259 |
| 3,933,236 A | * 1/1976 | Aterianus et al. | 198/32 |
| 4,119,120 A | 10/1978 | Mehaffy et al. | |
| 4,207,974 A | * 6/1980 | Dragotta | 198/344 |
| 4,728,501 A | 3/1988 | Atake | 422/100 |
| 4,944,924 A | * 7/1990 | Mawhirt et al. | 422/104 |
| 5,365,798 A | 11/1994 | Kressirer | 73/864.11 |
| 5,772,962 A | * 6/1998 | Uchida et al. | 422/67 |
| 6,001,310 A | * 12/1999 | Shaffer et al. | 422/102 |
| 6,148,878 A | * 9/2000 | Ganz et al. | 141/129 |

* cited by examiner

Primary Examiner—T. Tung
Assistant Examiner—Brian R. Gordon
(74) Attorney, Agent, or Firm—Womble Carlyle Sandridge & Rice, PLLC

(57) ABSTRACT

The invention disclosed provides a method and apparatus for mounting pre-cut capillary sized pipette tubes to aspiration tubes in a chemical processor. According to a first embodiment, the pipette tubes are dispensed from a magazine hopper into channels in a series of blocks that are connected to one another as a conveyor. The conveyor reorients the pipette tubes from horizontal to vertical to be engaged by the vertical aspiration tubes. According to a second preferred embodiment, the blocks are in the form of one or more trays that reciprocate between the hopper and the aspiration tubes. In both embodiments, the apparatus includes a clamp having a pair of closeable jaws adapted to grasp and remove the pipette tubes from the aspiration tubes after use.

21 Claims, 9 Drawing Sheets

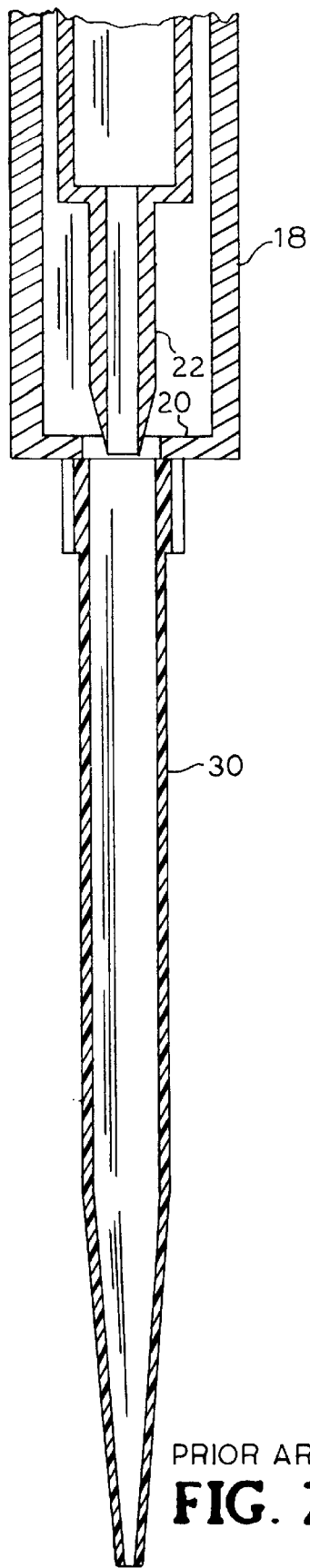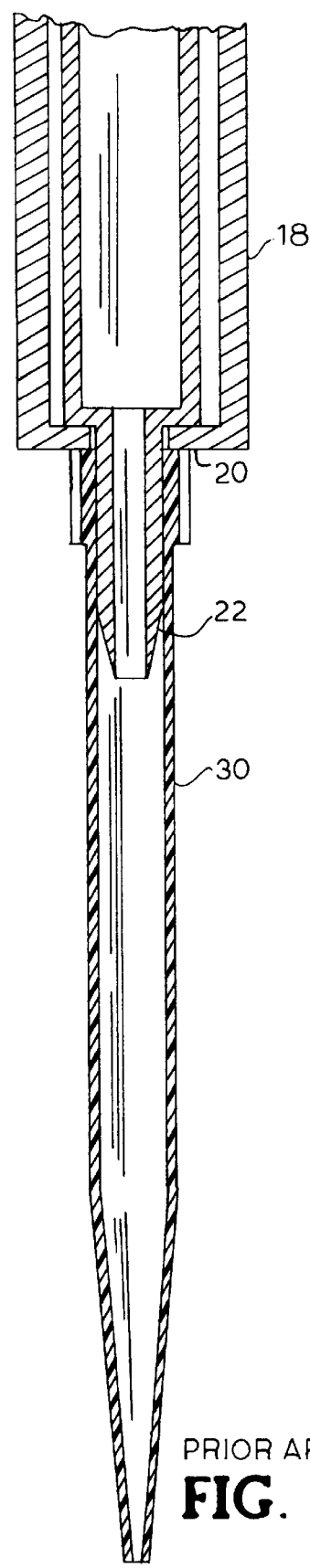
PRIOR ART
FIG. 2A
PRIOR ART
FIG. 2B

APPARATUS AND METHOD FOR CHEMICAL PROCESSING

BACKGROUND OF THE INVENTION

1. Field of the Invention

This invention relates to methods and apparatus for automatically combining chemical components and synthesizing compounds therefrom, and more particularly to methods and apparatus for mounting and discharging pipette tips in such apparatus.

2. Background and Related Art

Contemporary chemical research that is designed to create new and useful compounds for pharmaceutical applications no longer relies on the inspired chemist who employed knowledge, experience, and intuition to select the chemical components to be combined. The modern systems that are used to synthesize experimental compounds employ robotic equipment that is programmed to attempt all possible combinations and leave the selection process to be applied to the end results. By maximizing the number of chemical combinations attempted, more compounds are evaluated, and the chance of success becomes greater.

A robotic laboratory chemical processor that performs the described programmed robotic chemical compounding is supplied by TECAN® U.S., Post Office Box 13953, Research Triangle Park, North Carolina 27709, and is identified as the "GENESIS®" sample processor. The GENESIS® sample processor is able to automatically mount a set of up to eight molded, rack-mounted pipette tips onto nozzles that are each connected to a controlled aspiration-injection unit. The GENESIS® sample processor moves the pipette tips in a manner to transfer a measured quantity of a chemical component from a reservoir in a first position to a reaction site in a second position where they are combined with other components. The chemical combination is warmed and agitated according to a prescribed program to attempt to encourage a reaction between the components. The molded pipette tips are typically used only once and discarded in order to minimize the chance of cross contamination of the chemicals.

While it is important to discard used pipette tips to avoid contamination of one chemical to another, this practice is expensive and wasteful of materials. The molded pipette tips that are typically used are expensive when used in large numbers. Pipette tips are expensive because they are injection molded and they occupy a substantial amount of space. Thus, substitution of a simpler, more economical component for the known molded pipette tip could generate savings in money and materials. In addition, since the prior art molded pipette tips are fed to the robotic apparatus in a rack that requires space to store and regular refilling with pipette tips, other forms of pipette tip material, as disclosed below, provide further economy by eliminating the rack refilling operation. A form of pipette that is recognized by the present invention to be economical and effective for use in a robotic chemical sample processor is a pipette tube, i.e., a hollow cylindrical member with two open ends.

It is therefore an object of the present invention to provide pre-cut pipette tubes that can acquire a very small sample quantity and are able to be automatically mounted to pipette aspiration nozzles for use in a chemical sample processor.

It is a further object of the present invention to provide an apparatus to convey and mount the pre-cut pipette tubes of the invention to aspiration nozzles of a robotic sample chemical processor.

It is an additional object of the present invention to provide chemical sample processor pre-cut pipette tubes that are able to fit snugly into pipette engagement rings for use in a chemical sample processor.

These and other objects of the present invention will be better understood through the description and claims to follow.

SUMMARY OF THE INVENTION

The present invention provides an apparatus and method for chemical processing, comprising apparatus for conveying pre-cut pipette tubes to a position under a set of aspiration tubes and means for mounting the pipette tubes to the aspiration tubes in an automated chemical sample processor. In particular, the pre-cut pipette tubes are stored in a magazine hopper and dispensed to a transporter adapted for receiving and transporting individual pipette tubes. The transporter positions the pipette tubes for engagement by the aspiration tubes. Upon completing the sequence of steps for combining chemical components, the invention apparatus discharges the used disposable pipette tubes and is ready to begin a second cycle.

BRIEF DESCRIPTION OF THE DRAWINGS

The features and novel aspects of the invention disclosed will become apparent from the following description and accompanying drawings, where:

FIGS. 2A and 2B are enlarged partial cross sectional elevation views of a holder and pipette tip of the prior art showing a sequence of operations of the nozzle before engagement and as engaged with the pipette tip.

DETAILED DESCRIPTION OF PREFERRED EMBODIMENTS OF THE INVENTION

Figure 1:
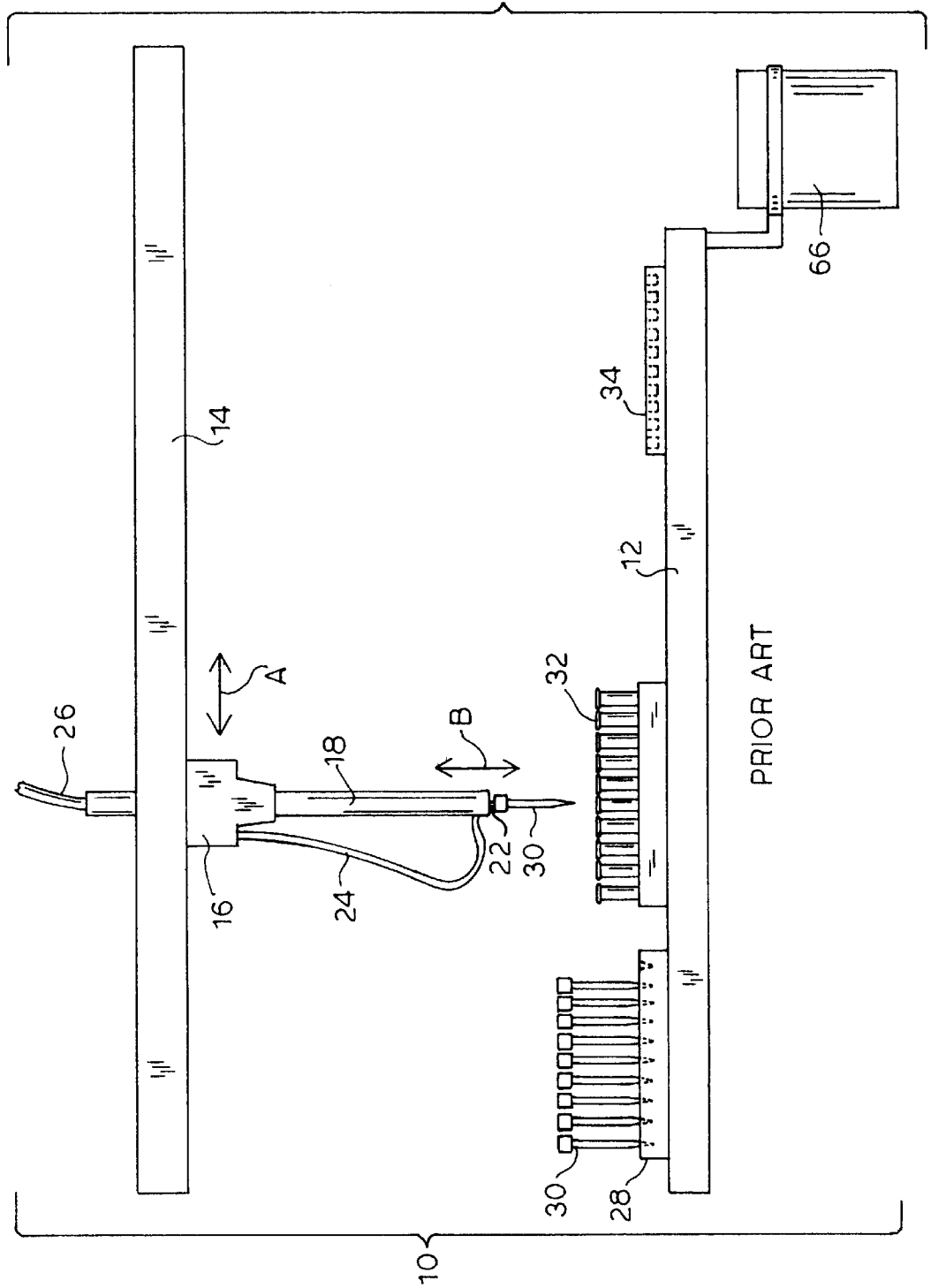
FIG. 1 is a schematic elevation view of a chemical sample processor apparatus of the prior art.

FIG. 1 is a schematic elevation view of a typical robotic chemical sample processor 10 known in the prior art. The operative portions of chemical sample processor 10 include table 12, that is supported horizontally on a frame (not shown), and track 14 that is horizontally mounted to the frame at a height above table 12. A carrier 16 is assembled to track 14 in a manner enabling carrier 16 to move horizontally along track 14 in the direction indicated by arrow A. Carrier 16 is moved along track 14 by a conveyor apparatus (not shown). A series of eight sheaths 18 (only one visible) vertically depend from carrier 16 in a linear array that is arranged perpendicular to the plane of FIG. 1. A mechanism (not shown) within carrier 16 moves individual sheaths 18 in a direction perpendicular to the plane of FIG. 1 to increase or decrease the spacing between adjacent sheaths 18. Sheaths 18 are moved vertically beneath carrier 16 in the direction indicated by arrow B. Thus, sheaths 18 are capable of three dimensional movement. An aspiration tube 26 is connected to a pressure control unit (not shown) and passes through the hollow center of sheath 18 to transmit controlled positive or negative pressure through nozzle 22 to pipette tip 30. A sensor connection 24 transmits signals to a system microprocessor (not shown) to indicate the presence or absence of a pipette tip 30 and a liquid chemical component therewithin. The movement of carrier 16 and the actions of sheaths 18 are controlled by the system microprocessor according to the requirements of the particular chemical process being performed.

Referring further to FIG. 1, rack 28 is mounted at a first position near the left end of table 12. Rack 28 supports in vertical orientation an array of molded pipette tips 30 in recesses in the top surface of rack 28 that are arranged in rows and columns. Rows of pipette tips 30 extend inward from the plane of FIG. 1 so that each sheath 18 is aligned with a column of pipette tips 30. Typically, the number of molded pipette tips 30 positioned in each row of rack 28 equals the number of sheaths 18 depending from carrier 16, for example 8. A number of individual reagent or sample supply reservoirs 32, each holding a specific chemical component, is mounted at a second position on table 12. A test grid 34 is mounted in a third position on table 12. Test grid 34 essentially comprises a plate broken into a plurality of sites for combining chemicals for reacting and analysis of results. Test grid 34 is formed, depending on the chemical experimentation to be performed, either as a flat plate, an array of test tubes, or an array of cavities for holding a small quantity of liquid. As illustrated, rack 28, reagent supply reservoirs 32, and test grid 34 are each mounted securely to table 12, but may be removed when necessary. FIG. 1 shows rack 28, reagent supply reservoirs 32, and test grid 34 aligned sequentially, but the apparatus described is capable of performing the described process steps with the positions of rack 28, reservoirs 32 and test grid 34 interchanged. Trash receptacle 66 is positioned beyond test grid 34 for discarding used pipette tips 30.

Enlarged FIGS. 2A and 2B illustrate a portion of the prior art apparatus of FIG. 1 during the sequence of steps by which nozzles 22, mounted within sheaths 18, move from non-engagement to engagement with molded pipette tips 30. FIGS. 2A and 2B are presented in enlarged cross sectional view for clarity. Each of the nozzles 22 is configured to engage a molded pipette tip 30 as described in detail below. Sheath 18, that is substantially cylindrical in configuration, terminates at its lower end with a stepped portion that is in contact with the upper end of molded pipette tip 30 throughout this operation. In FIG. 2A, nozzle 22 is fully retracted within sheath 18. While stepped portion 20 of sheath 18 remains in contact with molded pipette tip 30, nozzle 22 is caused to descend to engage pipette tip 30 in liquid-sealed assembly as seen in FIG. 2B. At the end of the chemical transfer cycle, the sample processor mechanism ejects molded pipette tip 30. The ejection procedure essentially follows the steps of FIGS. 2A and 2B in reverse, with molded pipette tip 30 being stripped from nozzle 22 by being pulled against stepped portion 20 by the retraction of nozzle 22 to within sheath 18. Then molded pipette tip 30 is allowed to drop into trash receptacle 66 (see FIG. 1). As noted above, the disposal of used molded pipette tips is considered necessary to prevent cross contamination of chemicals.

The operation of sample processor 10 is best described with further reference to FIG. 1. Carrier 16, controlled by a microprocessor (not shown), first moves to a position over rack 28. Sheaths 18, with nozzles 22 retracted, are lowered to be axially aligned to contact the upper end of each of a plurality of molded pipette tips 30 that are linearly arranged in rack 28. Each of the nozzles 22 is next extended beyond the end of sheath 18 to engage the upper end of respective molded pipette tip 30 as described with regard to FIGS. 2A and 2B. Sheaths 18 and nozzles 22 then move upwardly, carrying a set of molded pipette tips 30 with them. Carrier 16 next moves to position molded pipette tips 30 over the array of reagent supply reservoirs 32, and sheaths 18 descend a distance so that the lower end of molded pipette tip 30 enters the liquid contained in each of the respective reagent supply reservoirs 32. Sensors (not shown) are provided in nozzles 22 for detecting the presence of a pipette tip and a liquid, and for transmitting a responsive signal to the microprocessor, for example through sensor connection 24. The aspiration tube within sheath 18 connects nozzle 22 through tubing 26 with an air pressure control source (not shown). The air pressure control source is activated first for suctioning and subsequently for dispensing a sample quantity of chemical from respective supply reservoirs 32, typically on the order of 100 $\mu l$–300 $\mu l$ in volume. Sheaths 18 are raised to bring molded pipette tips 30 above the level of reagent supply reservoirs 32, and carrier 16 is moved to position each of the molded pipette tips 30 over a selected site on test grid 34. Sheaths 18 again descend, and the pressure in aspiration tubes 24 is increased so the chemical sample is deposited on a selected site on test grid 34. Next, sheaths 18 are raised an additional time and molded pipette tips 30 are moved away from test grid 34. Carrier 16 moves laterally to allow molded pipette tips 30 to be ejected into trash receptacle 66 as described above. Carrier 16 then travels back to its initial position over rack 28 to begin the process again.

While the process described above functions well, it is recognized that molded pipette tips take up valuable laboratory space and that large numbers of molded pipette tips are discarded thereby. As noted, the practice of discarding pipette tips is justified by the fundamental need to prevent contamination of chemicals. However, the present invention recognizes that the pipette tips merely function as a carrier tube that can be more simple in form, such as an extruded tube of uniform diameter, rather than a molded tip.

Improved spectroscopy and analytic methods now permit processing smaller samples than previously possible. By comparison, the quantity of reagent that can be accurately measured and transported by known pipette tips is a relatively large sample. This relatively large sample size requires storage space and mixing space for the chemical components. Use of a pipette tube, especially one having a capillary size bore, provides for acquisition and transport of much smaller measured quantities of reagent.

Figure 3:
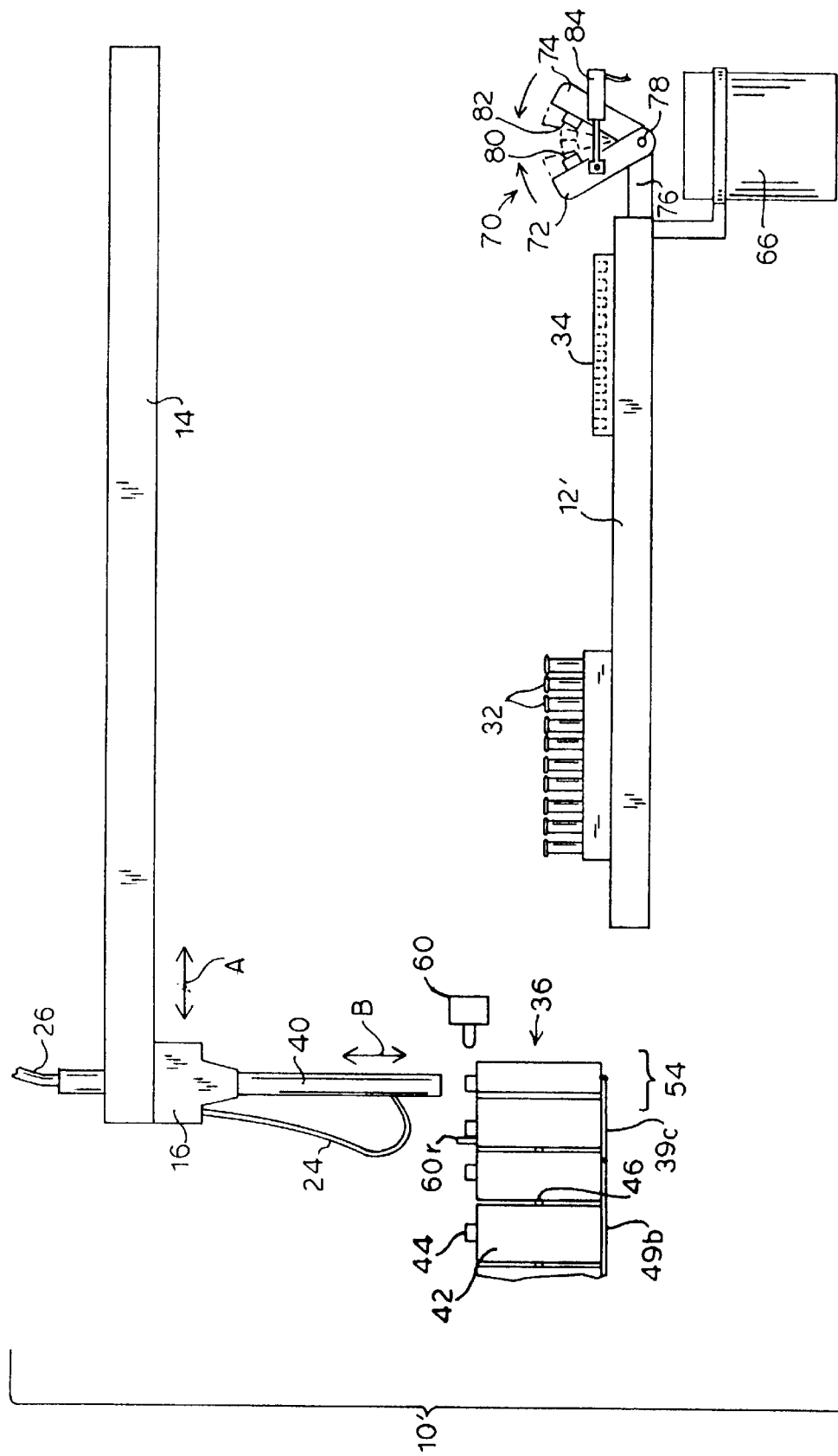
FIG. 3 is a schematic elevation view of a first embodiment of the invention.

Referring now to FIG. 3, the chemical sample processor 10' according to the first embodiment of the present invention is illustrated in a schematic elevation view. Chemical sample processor 10' of the invention includes features common to the prior art processor 10 of FIG. 1, including table 12' supporting reagent supply reservoir 32 and test grid 34 in sequential relation. However, table 12' of the invention does not hold a rack of pipette tips. Track 14 is mounted parallel to and above table 12' to guide carrier 16 in a direction shown by arrow A.

A series of aspiration tubes 40 depend from and are carried by carrier 16. Aspiration tubes 40 are moveable in direction A with carrier 16, in vertical direction B, and in a horizontal direction perpendicular to the plane of FIG. 3 to vary the spacing therebetween as required to pick up and deposit chemical components. Aspiration tubes 40 are adapted to engage pipette tubes 44 of the invention with an internally mounted resilient washer 41, as will be described below in regard to FIGS. 6A, 6B. Sensor connection 24 connects from sensors (not shown) located in the lower portion of aspiration tubes 40 to transmit signals to the system microprocessor. The sensors are adapted to detect the presence of a pipette and a liquid, when required. According to the present invention, a series of pre-cut pipette tubes 44 are carried in blocks 42 on a transporter, e.g. conveyor 36, that circulates horizontally to beneath aspiration tubes 40. A detector, e.g., photocell 60 and reflector 60r, are positioned to verify the presence of a pipette tube in each block 42. Site 54 represents the location at which aspiration tubes 40 pick up pipette tubes 44 for processing, shown in detail in FIGS. 4 and 5C.

Referring still to FIG. 3, the right end of table 12' has been modified to mount clamp 70 thereto by means of support arm 76. Clamp 70 has a pair of opposed jaws 72 and 74 that extend in a pair of planes that are each perpendicular to the plane of the illustration and at an arbitrary angle to each other. Jaws 72 and 74 are pivotably mounted to arm 76 and to each other at pivot pin 78 and are actuated to close and open by the action of a linear motion device, such as piston 84, operated by appropriate utilities. The facing surfaces of jaws 72 and 74 each mount a matching gripper 80 and 82 that are configured to matingly engage a set of pipette tubes 44 inserted therebetween. Grippers 80 and 82 are formed of a resilient polymeric material capable of frictionally gripping pipette tubes 44, such as a silicone rubber material.

Figure 4:
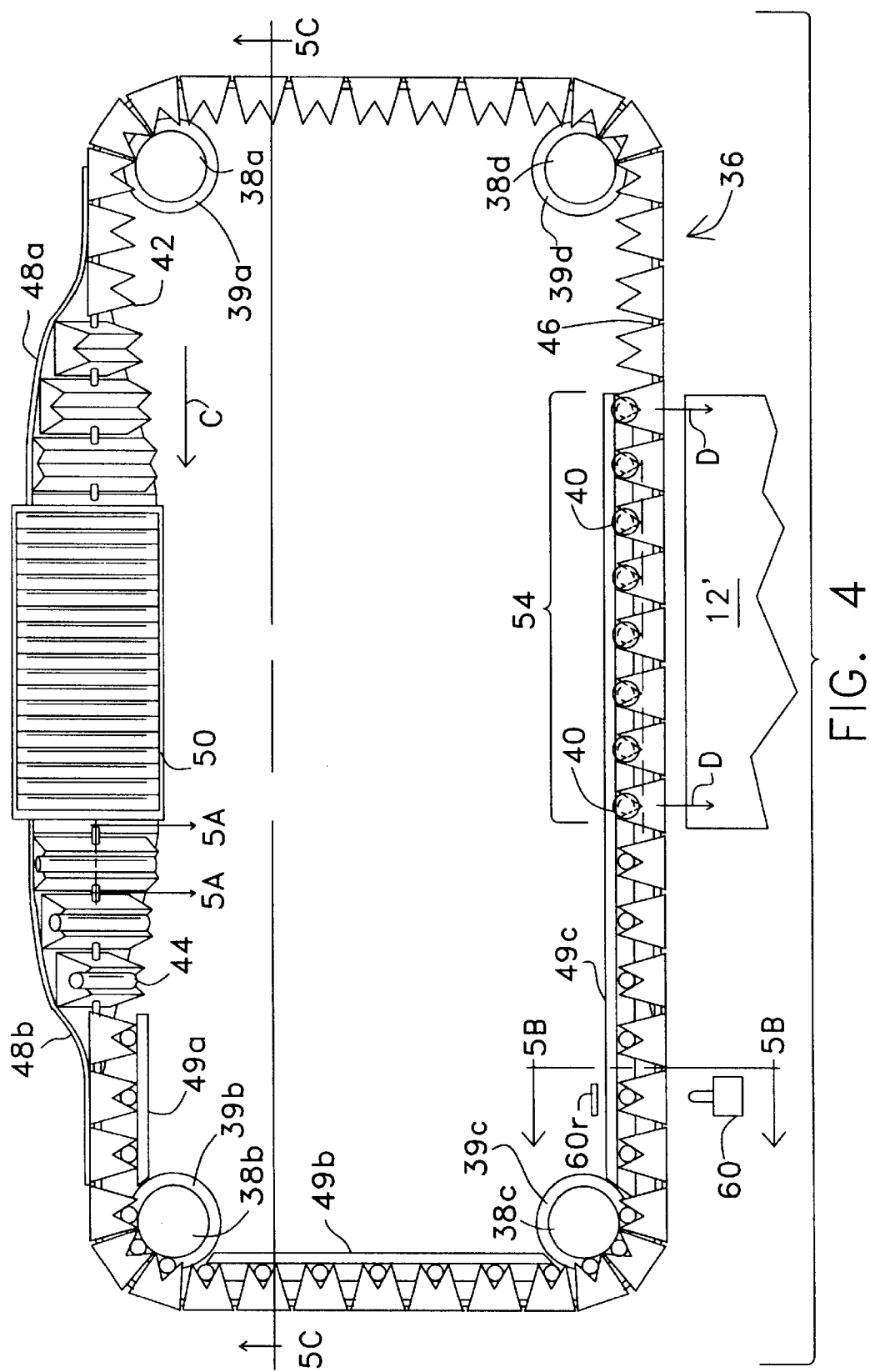
FIG. 4 is a top plan view of a conveyor for use in transporting pre-cut pipette tubes according to the first embodiment of the invention.

FIG. 4 illustrates a top plan view of a conveyor 36 as it is operationally mounted adjacent table 12'. Conveyor 36 includes a plurality of rotatable drums 38. In the preferred embodiment of the invention, four drums 38a, 38b, 38c, and 38d are provided at respective corners of a rectangular conveyor path. Each drum 38a, 38b, 38c, 38d is formed with a lower flange 39a, 39b, 39c, 39d to support respective tubes 44 in blocks 42. One of drums 38, e.g., drum 38a, is driven by a motor (not shown) to cause conveyor 36 to move in the direction shown by arrow C. Conveyor 36 comprises a series of blocks 42 that are connected to one another by connective rotatable members, e.g., links 46, described in detail below. Blocks 42 are pivotable about links 46 to be able to rotate from vertical to horizontal orientation as needed. Conveyor 36 passes a transfer site 54 on the end of its travel cycle closest to table 12' and passes hopper 50 on the opposite end of its travel cycle.

According to the present invention, pipette tubes 44 employed are extruded capillary-size tubes (having a bore sufficiently small that a given liquid will rise within the tube by force of surface tension). The shape of a pipette tube, having a substantially constant cross section throughout its length differs from that of the prior art molded pipette tip in which one end is substantially tubular and the other end is conical, terminating in a narrow opening. Pipette tubes 44 are pre-cut to a selected length, e.g., 40 mm, the length being determined according to the amount of liquid chemical to be acquired and transported. A greater degree of liquid volume control is attained by use of air pressure control (not illustrated) connected to pipette tube 44 through aspiration tube 40 (see FIG. 3). As will be understood, an increase of air pressure, or a restriction of the volume of air connected to the capillary tube, will reduce the amount of liquid acquired by the capillary. Conversely, a decrease of air pressure will increase the amount of liquid the capillary tube picks up. A device that is satisfactory for incremental, controlled pressure and volume control is a plunger in a cylinder, e.g., a syringe. Conveyor 36 is moved in the direction indicated by arrow C to pass drum 38a. Next, conveyor 36 contacts rotator plate 48a to rotate each block 42 from vertical to horizontal orientation. Blocks 42 pass below hopper 50 while they are horizontal.

Figure 5B:
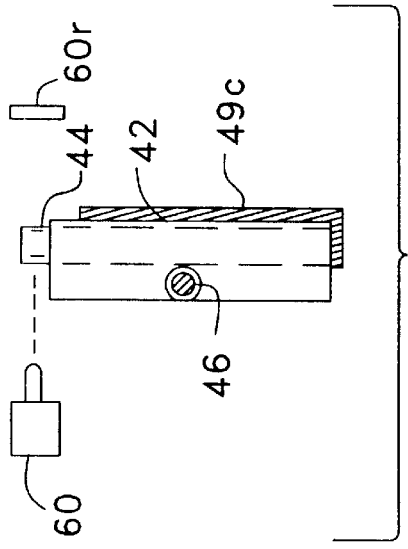
FIG. 5B is an enlarged cross sectional view of the conveyor showing the typical block of which the conveyor of FIG. 4 is formed and showing a pipette tube retainer plate and a photocell detector device.
Figure 5A:
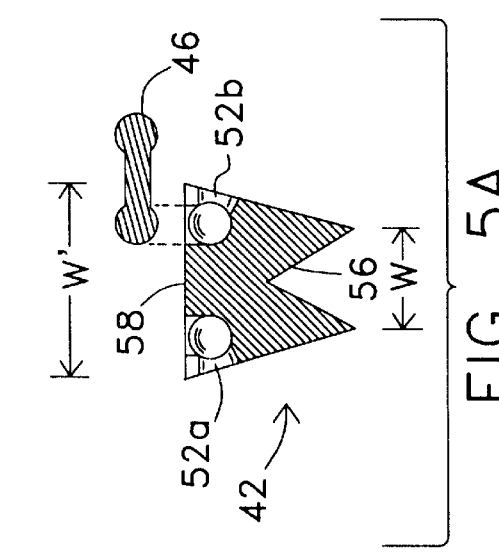
FIG. 5A is an enlarged cross sectional view of a connectable block and connecting link of the conveyor of FIG. 4 taken in the direction of line 5A—5A of FIG. 4.

As illustrated in FIG. 5A, block 42 is formed as a modified trapezoid with its "V" shaped inner channel 56 having a maximum width W and its outer surface having a width W', with width W' being greater than width W. Channels 56 are formed in a "V" cross section to positively support the cylindrical shape of pipette tubes 44, allowing for slight variations in diameter thereof. In this manner, blocks 42 are able to curve around drum 38a, 38b, 38c, and 38d without binding (see FIG. 4). Typical block 42 has socket 52a on a first side and socket 52b on a second side in axial alignment with each other. Sockets 52a and 52b are each sized to receive a respective bead end of link 46 in pivotable engagement, with multiple such blocks 42 so connected to form conveyor 36. Sockets 52a and 52b are formed to allow link 46 to pivot freely in a plane perpendicular to inner channel 56.

Figure 5C:
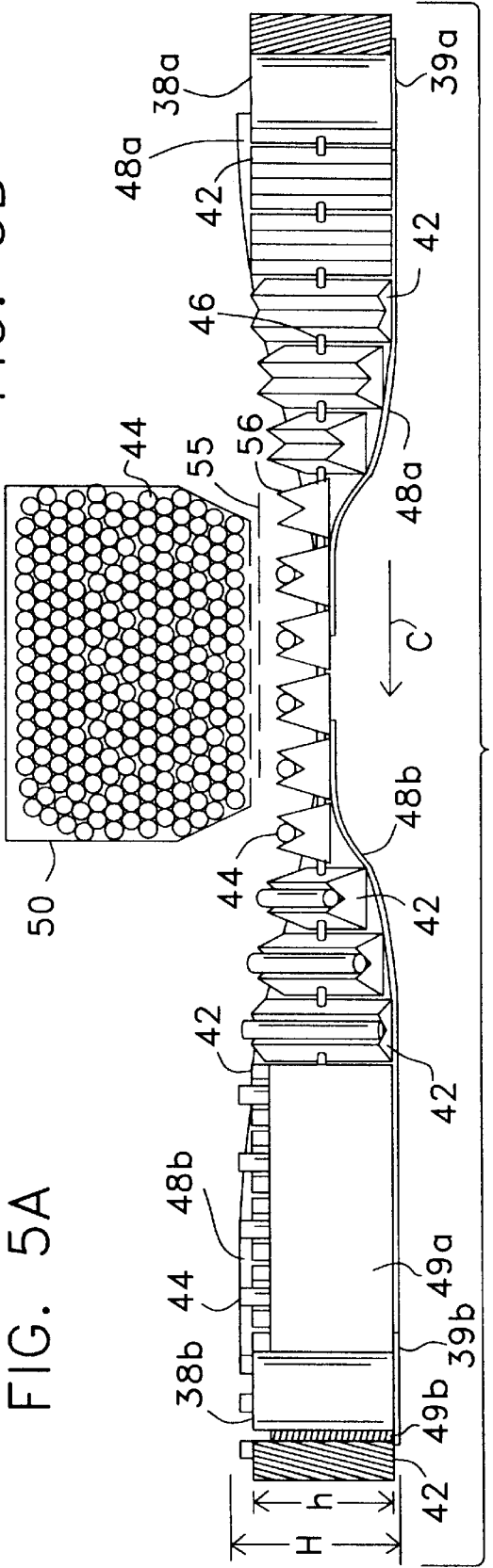
FIG. 5C is a cross sectional view of a portion of the conveyor taken in the direction of line 5C—5C of FIG. 4.

Referring now to FIG. 5C, showing a cross section elevation view of conveyor 36 with hopper 50 positioned over a portion of conveyor 36. Hopper 50 is of the magazine type, adapted to store and dispense a multiplicity of elongate objects, e.g. pipette tubes, of similar length in horizontal orientation. Hopper 50 is provided with a multiple slot gating mechanism 55, as is known, adapted to dispense individual pre-cut pipette tubes 44 as needed to inner channel 56 in each block 42 in spaced apart relation. In the section of conveyor 36 shown in FIG. 5C, blocks 42 are moved in the direction of arrow C and are turned from a vertical orientation adjacent drum 38a on the right, to a horizontal orientation below hopper 50, to a vertical orientation adjacent drum 38b on the left. Drums 38a, 38b, 38c, 38d are formed with flanges 39a, 39b, 39c, 39d at their lower ends that is adapted to support blocks 42 and keep pipette tubes 44 from falling. Blocks 42 are turned by contact with guide plates 48a and 48b. Typical guide plate 48a of the invention is formed as a 90° helix from a vertical plane adjacent right end drum 38a to a horizontal plane adjacent hopper 50 to contact and turn blocks 42 accordingly. Conversely, guide plate 48b is formed as a reverse helix to provide a transition from a horizontal plane adjacent hopper 50 to a vertical plane adjacent left drum 38b. Retainer plate 49c (see FIG. 5B) and retainer plate 49b (see FIG. 5C) each have a horizontal supporting lip at their lower portion configured to hold pipette tubes 44 from dropping down while they are transported in vertical orientation. Retainer plate 49a extends along conveyor 36 from hopper 50 to drum 38b. Retainer plate 49b extends along conveyor 36 between drums 38b and 38c; retainer plate 49c extends along conveyor 36 between drum 38c and transfer site 54.

FIG. 5B, taken as a section between adjacent blocks 42 of conveyor 36, shows the manner in which retainer plate 49c supports tube 44 horizontally and vertically in block 42.

Referring back to FIG. 4, blocks 42 of conveyor 36 are empty between transfer site 54 and hopper 50; and carry tubes 44 from hopper 50 to transfer site 54, as viewed in the direction indicated by arrow C. As each block 42 passes photocell 60 and reflector 60r, the presence of a pipette tube 44 is checked and transmitted to the system microprocessor.

The microprocessor simultaneously coordinates the pipette tube information with each block 42 passing photocell 60 to determine when a selected number of sequential blocks, e.g. eight, all have pipette tubes 44. Assurance of a pipette tube in each block guarantees that no chemical test is missed. When the microprocessor has determined that eight successive blocks 42 contain pipette tubes 44, the eight aspiration tubes 40 are lowered to engage and lift pipette tubes 44 as described more fully below. After aspiration tubes 40 lift pipette tubes 44, aspiration tubes 40 are moved in the direction indicated by arrows D to the vicinity of reagent supply reservoirs 32 (see FIG. 3). By not providing a retainer plate 49 in the portion of conveyor 36 beyond transfer station 54, and by leaving the lower portion of inner channel 56 open, any pipette tubes 44 that have not been engaged and lifted by aspiration tubes 40 (see FIG. 3) at transfer site 54 will be allowed to fall, clearing inner channel 56. A new tube 44 will be deposited in channel 56 at hopper 50.

Figure 6A:
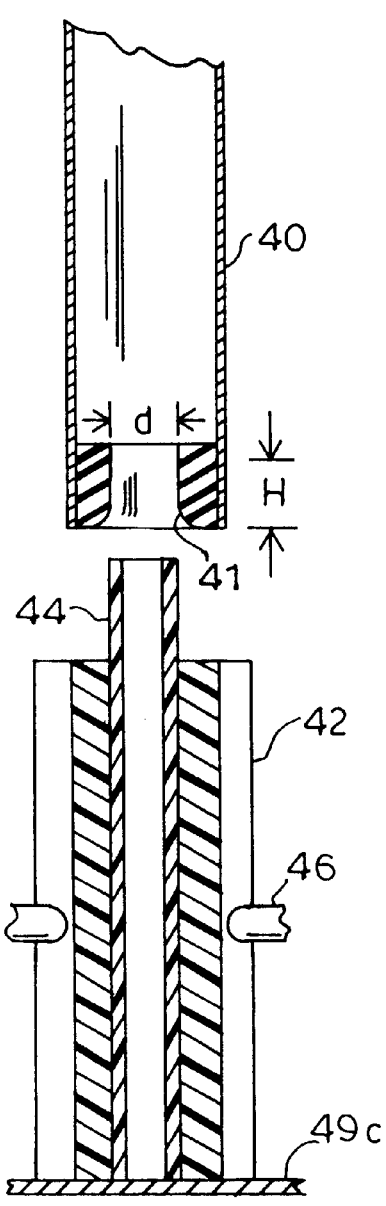
FIGS. 6A and 6B are enlarged partial cross sectional elevation views showing a sequence of operations of a nozzle before engagement and as engaged with a pre-cut pipette tube according to the present invention.
Figure 6B:
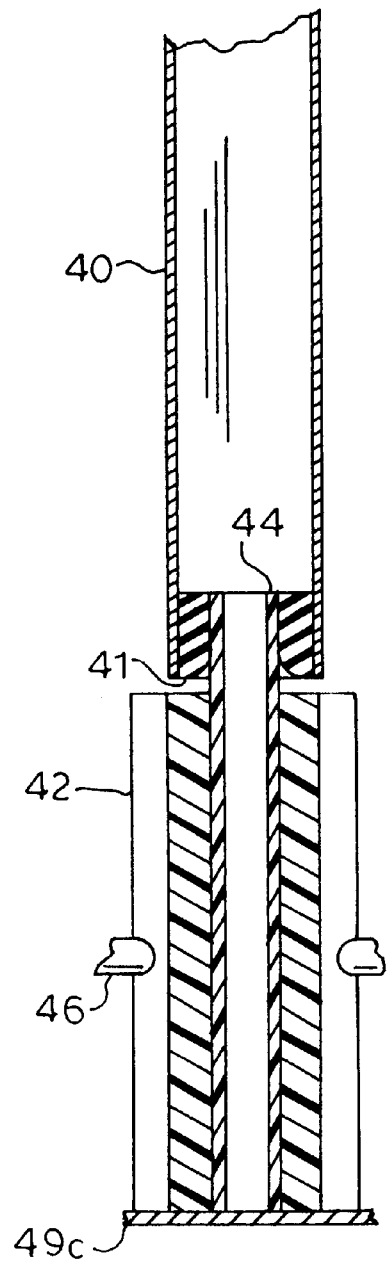

Referring now to FIGS. 6A and 6B, the engagement sequence between aspiration tubes 40 and pipette tubes 44 is shown in two steps. In FIG. 6A, pipette tube 44 is supported vertically by retainer plate 49*c* in block 42. The upper end of pipette tube 44 resides slightly below the bottom of aspiration tube 40. The lower end of aspiration tube 40 includes a resilient washer 41 with a bell-shaped entry portion. The internal diameter d of washer 41 is sized to snugly fit the outside of pipette tube 44 in liquid-tight communication. The height H of washer 41 is greater than the inside diameter d to provide a stable engagement for pipette tube 44. In FIG. 6B, aspiration tube 40 has been lowered so its lower end, and particularly washer 41, engages pipette tube 44 for acquiring liquid and operation.

As illustrated in FIG. 3, sample processor 10' operates similarly to the steps described above with respect to the prior art chemical processor, with pipette tubes 44 being positioned by hopper 50 feeding pipette tubes 44 to conveyor 36. The chemical sample processor 10' then goes through the steps of mounting pipette tubes 44 to aspiration tubes 40, acquiring a chemical component from reagent supply reservoirs 32, and depositing the chemical component onto test grid 34. Upon completion of these steps, carrier 16 moves to the right end of table 12' so that pipette tubes 44 are positioned above the approximate center of a clamp 70. Next, aspiration tubes 40 are moved downward so that pipette tubes 44 are positioned between grippers 80 and 82. Jaws 72 and 74 are pivoted together by piston 84 so that grippers 80 and 82 grasp pipette tubes 44. Aspiration tubes 40 are moved upward so that pipette tubes 44 are extracted from washer 41 (see FIGS. 6B and 6A) and held between grippers 80 and 82. Piston 84 is next reversed so that jaws 72 and 74 open and pipette tubes 44 that have been held therebetween are released to drop into trash receptacle 66. Next, carrier 16 moves to the left to begin a new cycle.

Figure 7:
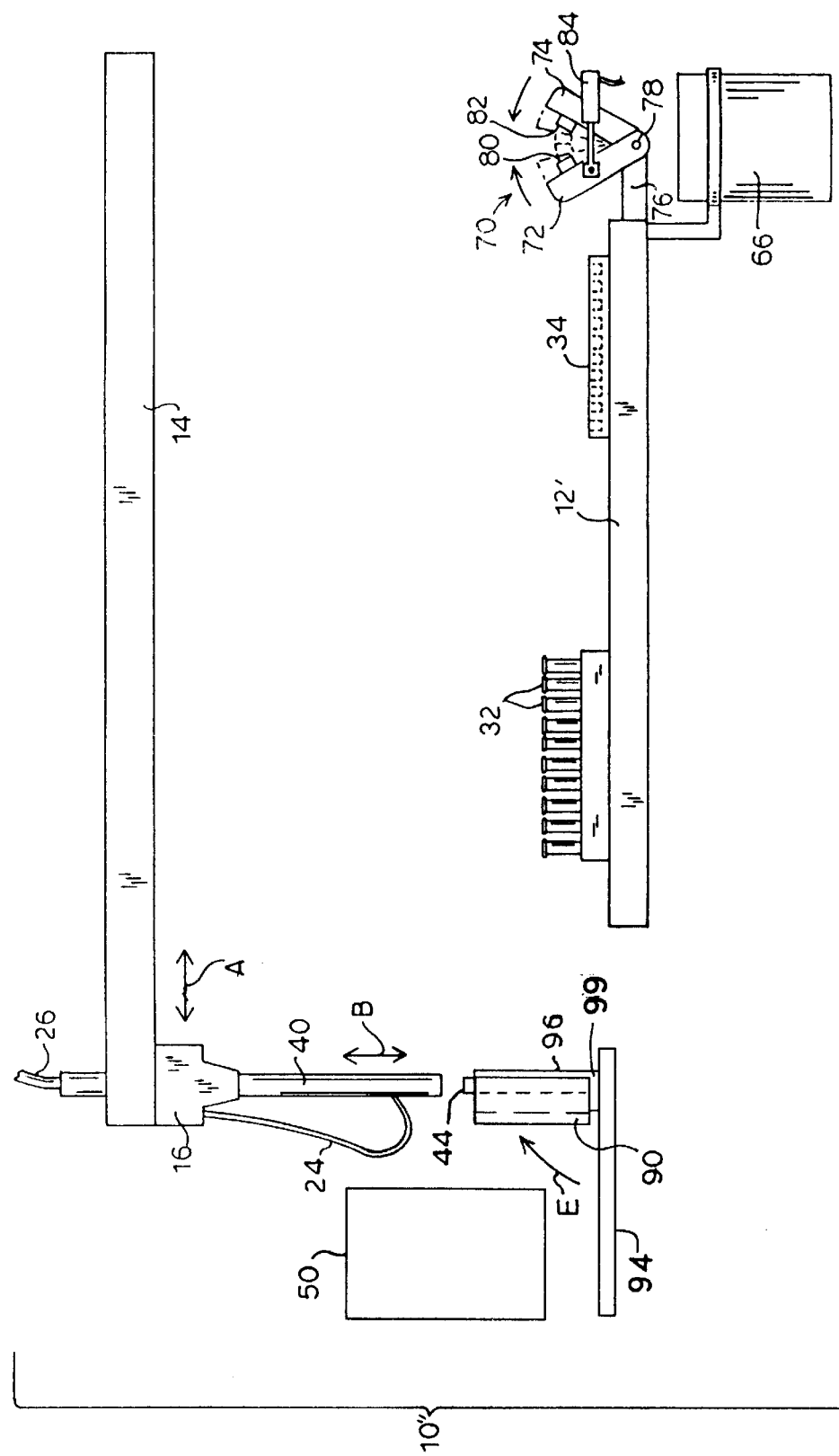
FIG. 7 is a schematic elevation view of a second embodiment of the invention.

The second embodiment of the invention is seen in elevation side view in FIG. 7, with details of the operational steps involved shown in FIGS. 8A–8D. Referring now to FIG. 7, chemical sample processor 10" comprises table 12', having supply reservoirs 32, test grid 34 and clamp 70 mounted thereon, and track 14, carrier 16, and aspiration tubes 40 positioned thereabove. Table 12', supply reservoirs 32, test grid 34, clamp 70, track 14, carrier 16, and aspiration tubes 40 were each described in detail above. Magazine hopper 50 (seen in end elevation view) stores a quantity of pipette tubes for transfer to a transporter, e.g., tray 90. Tray 90 is configured to pivot from horizontal to vertical in the direction shown by arrow E after being loaded as described below. Pipette tubes 44 are held in vertical alignment beneath aspiration tubes 40 for engagement thereby.

FIGS. 8A–8D depict the sequence of operations in which pipette tubes 44 are moved from hopper 50 to tray 90. Hopper 50 stores pipette tubes 44 in horizontal orientation from which they are released by gate 55 when tray 90 is positioned thereunder. When filled with pipette tubes 44, tray 90 moves and pivots to axially align pipette tubes 44 with aspiration tubes 40.

Figure 8A:
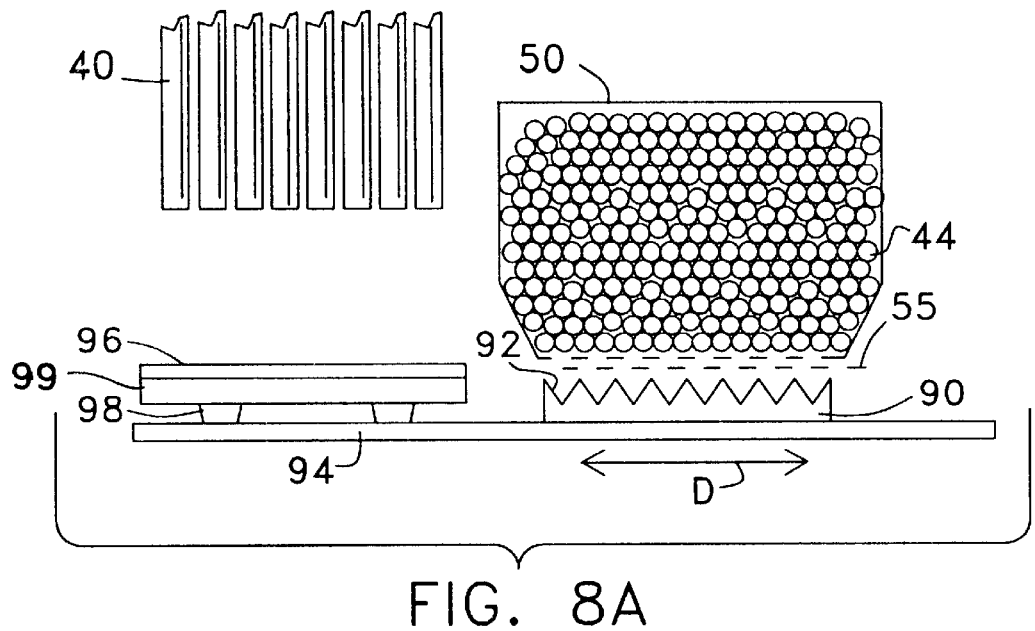
FIGS. 8A–8D are a series of schematic elevation views depicting the steps in which cut pipette tubes are dispensed from a magazine hopper to a grooved tray which moves and pivots the pipette tubes for engagement by aspiration tubes.

In FIG. 8A, tray 90 is positioned at the extreme right end of its travel along track 94 in the direction indicated by arrow D so as to be beneath magazine hopper 50 (seen in front elevation view). Channels 92, formed as a substantially parallel series of "V" shaped grooves in the upper surface of tray 90, are substantially aligned to accept pipette tubes 44 from multi-slotted gate 55. As noted above in reference to the first embodiment of the invention, it is preferred to form channels 92 in a "V" shape to accommodate minor differences in the diameter of cylindrical pipette tubes 44.

Figure 8B:
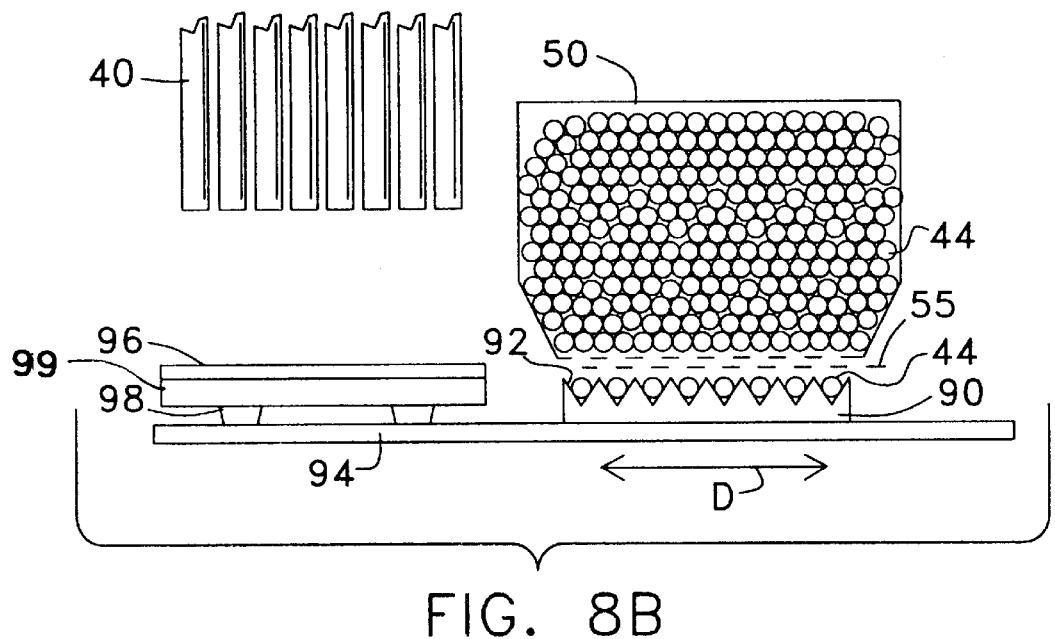

FIG. 8B shows the mechanism of the second embodiment after pipette tubes 44 have been dispensed from magazine hopper 50 through gate 55 into channels 92 of tray 90. Since chemical sample processor 10" includes a plurality of aspiration tubes 40, e.g. eight, tray 90 is similarly formed with eight channels 92. The invention recognizes that gate 55 could be formed with a lesser number of slots, e.g. one or four, wherein the invention mechanism would be adapted to move tray 90 to an appropriate number of positions to fill channels 92. Sensor means (not shown) is provided to ensure that each channel 92 contains a pipette tube 44.

Figure 8C:
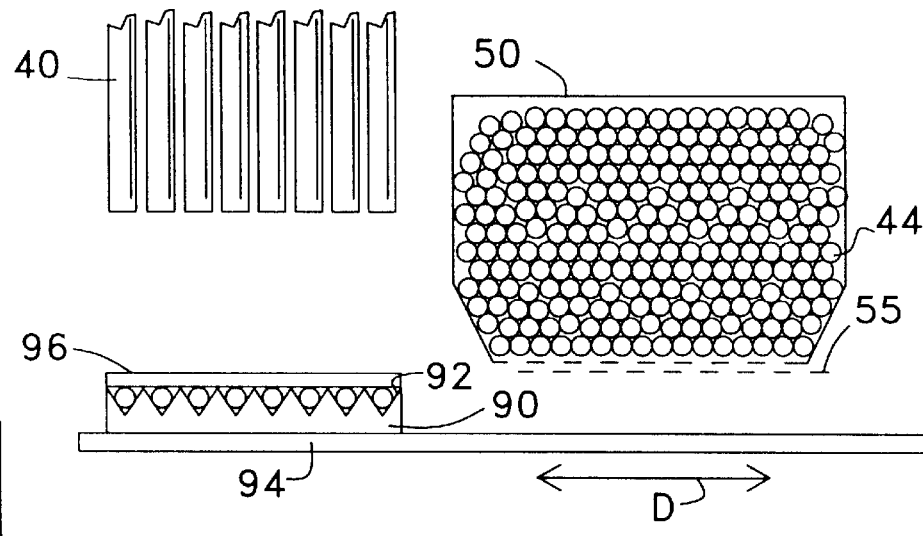

Once channels 92 have been filled with pipette tubes 44, tray 90 is moved to the left along track 94, as illustrated in FIG. 8C. At the left end of its travel, tray 90 is positioned beneath cover 96 so that cover 96 encloses the top and lip 99 encloses the rear of channels 92 to contain pipette tubes 44 therewithin. With tray 90 under cover 96, pipette tubes 44 are aligned beneath aspiration tubes 40, albeit in horizontal orientation.

Figure 8D:
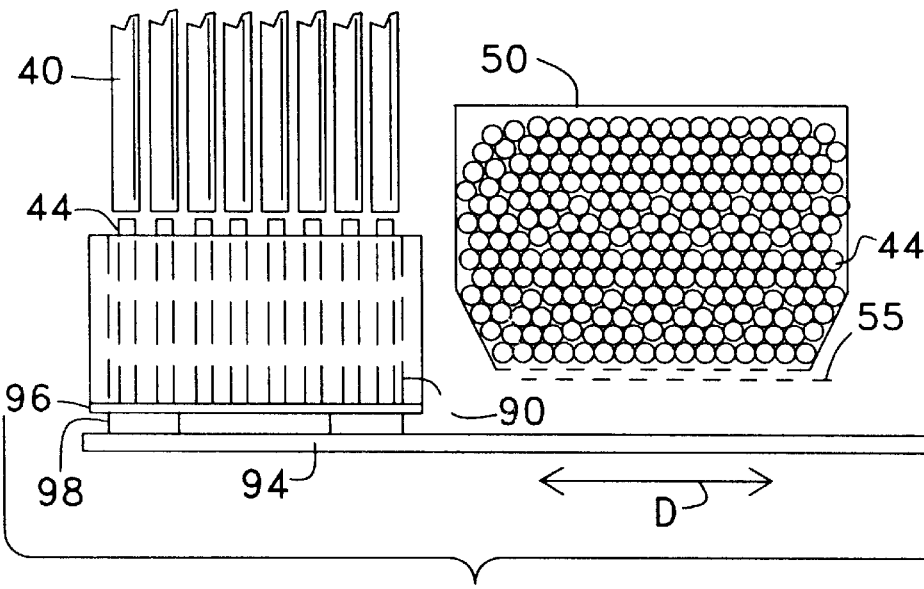

As seen best in FIGS. 8A and 8B, cover 96 is mounted on a pair of hinges 98 so as to be pivotable from horizontal to vertical in the direction indicated by arrow E (see FIG. 7). When tray 90 has been moved beyond the left end of magazine hopper 50 and tray 90 is covered by cover 96, tray 90 and cover 96 are pivoted from horizontal to vertical by any known mechanism, e.g., a pneumatic cylinder. The position of tray 90 and cover 96 enclosing pipette tubes 44 is illustrated in FIG. 8D, pipette tubes 44 being axially aligned beneath aspiration tubes 40. As shown in FIG. 7 and FIGS. 8A and 8B, cover 96 includes lip 99 on one side thereof to keep pipette tubes 44 from dropping out of channels 96; when aligned vertically as seen in FIG. 8D, lip 99 is below pipette tubes 44.

Once pipette tubes 44 have been engaged by aspiration tubes 40 and lifted from channels 96, tray 90 follows a reverse series of steps as depicted in FIGS. 8C, 8B, and 8A, in sequence, to be in position for being reloaded with a further set of pipette tubes 44.

An alternate arrangement that retains the principles of this second embodiment of the invention is to provide a second tray 90' that would be situated so as to reciprocate with first tray 90, placing first tray 90 beneath first magazine hopper 50 in a first cycle, while second tray 90' resides beneath aspiration tubes 40. When channels 92 in first tray 90 are filled and pipette tubes 44 have been removed from second tray 90' (not shown), each of first tray 90 and second tray 90' will shift, e.g., left, and emptied second tray 90' will be positioned horizontally beneath a second hopper 50' (not shown).

Thus, the present invention provides a method and apparatus used with a chemical sample processor for supplying and mounting pre-cut pipette tips of a selected length. As described above, the present invention provides an improved apparatus for the automatic processing of chemical samples by the use of pre-cut, rather than molded, pipette tubes. The benefits include savings in labor, savings in material cost, selection of tip length, and savings in space. The specific embodiments and examples described above are for purposes of illustration and are not to be construed as limiting the principle or scope of the present invention, which is best understood in relation to the claims to follow.

What is claimed is:

1. A method for dispensing and engaging a plurality of pipette tubes in a chemical sample processor, comprising the steps of:

(a) storing a plurality of pipette tubes in a magazine hopper;

(b) dispensing the pipette tubes in a substantially horizontal orientation from the magazine hopper to a transporter;

(c) moving the pipette tubes to a transfer site for engagement by a plurality of aspiration tubes being conveyed by a carrier;

(d) re-orienting the pipette tubes from the substantially horizontal orientation to a substantially vertical orientation; and (e) engaging and lifting the pipette tubes with the plurality of aspiration tubes.

2. The method of claim 1, further comprising detecting the presence of the pipette tubes in the transporter; and transmitting a signal related thereto to a microprocessor.

3. The method of claim 1, further comprising grasping the pipette tubes and removing the pipette tubes from the aspiration tubes.

4. A method for chemical sample processing, comprising the steps of:

(a) storing a plurality of pre-cut pipette tubes in a magazine hopper;

(b) dispensing the pre-cut pipette tubes in substantially horizontal orientation from the magazine hopper into a transporter;

(c) moving the pre-cut pipette tubes from the magazine hopper to a transfer site for engagement by a plurality of aspiration tubes;

(d) re-orienting the pre-cut pipette tubes from the substantially horizontal orientation to a substantially vertical orientation;

(e) engaging and lifting the pre-cut pipette tubes with the aspiration tubes;

(f) moving the pre-cut pipette tubes to a chemical reagent reservoir site and suctioning a sample of chemical sample into each of the pre-cut pipette tubes;

(g) moving the pre-cut pipette tubes with the chemical samples to a test grid and dispensing the chemical samples onto selected sites on the test grid;

(h) moving the pre-cut pipette tubes to a clamp and grasping the pre-cut pipette tubes with the clamp while elevating the aspiration tubes to disengage the pre-cut pipette tubes therefrom; and (i) returning the aspiration tubes to the hopper.

5. The method for chemical sample processing of claim 4, further comprising the step of detecting the presence of the pre-cut pipette tubes and transmitting a signal related thereto to a microprocessor.

6. A chemical sample processor, comprising:

(a) a carrier having a plurality of aspiration tubes received thereon, wherein each aspiration tube has an upper end and a lower end;

(b) a magazine hopper for dispensing a plurality of pipette tubes;

(c) a transporter mounted below the magazine hopper and configured to receive the plurality of pipette tubes from the magazine hopper in a substantially horizontal orientation and spaced apart from one another, wherein the transporter is operative to move the plurality of pipette tubes thereon and to turn the plurality of pipette tubes from a substantially horizontal to a substantially vertical orientation so as to position the plurality of pipette tubes for being individually engaged by the plurality of aspiration tubes.

7. The chemical sample processor of claim 6, and wherein the plurality of pipette tubes comprises a plurality of pre-cut pipette tubes disposed in the magazine hopper.

8. The chemical sample processor of claim 7, further comprising a means for keeping the plurality of pipette tubes in contact with the transporter until the pipette tubes are engaged by the aspiration tubes.

9. The chemical sample processor of claim 8, wherein the means for keeping a plurality of pipette tubes in contact with the transporter comprises a retainer plate.

10. The chemical sample processor of claim 9, wherein the retainer plate includes a supporting lip.

11. The chemical sample processor of claim 6, wherein each of the aspiration tubes further comprises a resilient washer having a bore for receiving a pipette tube.

12. The chemical sample processor of claim 11, wherein the resilient washer has a bell-shaped entry portion.

13. The chemical sample processor of claim 11, wherein the resilient washer is mounted to the lower end of the aspiration tube.

14. The chemical sample processor of claim 6, wherein the transporter comprises a conveyor having a plurality of blocks connected to each other by a series of links.

15. The chemical sample processor of claim 14, wherein each of the blocks is pivotable about the links between a substantially vertical orientation and a substantially horizontal orientation.

16. The chemical sample processor of claim 6, wherein the transporter comprises a tray having a series of substantially parallel channels formed in one surface thereof, wherein the channels are configured to receive the pipette tubes.

17. The chemical sample processor of claim 16, further comprising a cover adapted to engage the tray so as to retain the pipette tubes in the channels when the tray is in a substantially vertical orientation.

18. The chemical sample processor of claim 16, wherein the tray and the cover are moveably connected by a hinge.

19. The chemical sample processor of claim 6, further comprising a detector for determining the presence of a pipette tube in the transporter.

20. The chemical sample processor of claim 19, wherein the detector comprises a photocell.

21. The chemical sample processor of claim 6, further comprising a clamp adapted for grasping the pipette tubes.

* * * * *